United States Patent [19]

Mera

[11] Patent Number: 4,898,587
[45] Date of Patent: Feb. 6, 1990

[54] INTRAVENOUS LINE STABILIZING DEVICE

[76] Inventor: Csaba L. Mera, 1025 E. Ocean Ave., Suite B, Lompoc, Calif. 93436

[21] Appl. No.: 271,618

[22] Filed: Nov. 15, 1988

[51] Int. Cl.$^4$ ............................................. A61M 5/32
[52] U.S. Cl. ................................... 604/174; 604/180; 128/DIG. 26
[58] Field of Search ................ 604/174, 180; 128/133, 128/DIG. 26, 348

[56] References Cited

U.S. PATENT DOCUMENTS

| | | |
|---|---|---|
| 3,630,195 | 12/1971 | Santomieri . |
| 3,696,920 | 10/1972 | Lahay . |
| 3,826,254 | 7/1974 | Mellor . |
| 3,834,380 | 9/1974 | Boyd . |
| 4,165,748 | 8/1979 | Johnson . |
| 4,224,937 | 9/1980 | Gordon . |
| 4,250,880 | 2/1981 | Gordon . |
| 4,316,461 | 2/1982 | Marais et al. . |
| 4,333,468 | 6/1982 | Geist . |
| 4,380,234 | 4/1983 | Kamen . |
| 4,449,975 | 5/1984 | Perry . |
| 4,669,458 | 6/1987 | Abraham et al. . |
| 4,690,675 | 9/1987 | Katz . |
| 4,702,736 | 10/1987 | Kalt et al. . |

FOREIGN PATENT DOCUMENTS 265159  4/1988  European Pat. Off. ............ 604/174

Primary Examiner—John D. Yasko
Attorney, Agent, or Firm—Kelly, Bauersfeld & Lowry

[57] ABSTRACT

A device for affixing a medical tube, such as an intravenous line, to a part of a body includes a base plate which is contourable to the shape of the body, cushioned straps which secure the medical tube to the base plate, and a cover which overlies the base plate and a portion of the tube. The base plate is provided a pair of limbs which adjoin one another at a crotch, but which are otherwise equidistantly spaced from one another for positioning astride each side of a vein. The cover is adhesively secured to the base plate to form a continuous bridging surface between the limbs, and includes a sealed air compartment which provides a cushion for shielding covered portions of the medical tube from externally applied impact forces. The medical tube is secured within a tapered channel on the upper surface of the base plate, which aligns the tube with the base plate crotch. The intravenous line stabilizing device securely positions the medical tube adjacent a catheter injection site in a manner which minimizes relative movement of the catheter and the vein.

22 Claims, 2 Drawing Sheets

U.S. Patent Feb. 6, 1990 Sheet 1 of 2 4,898,587
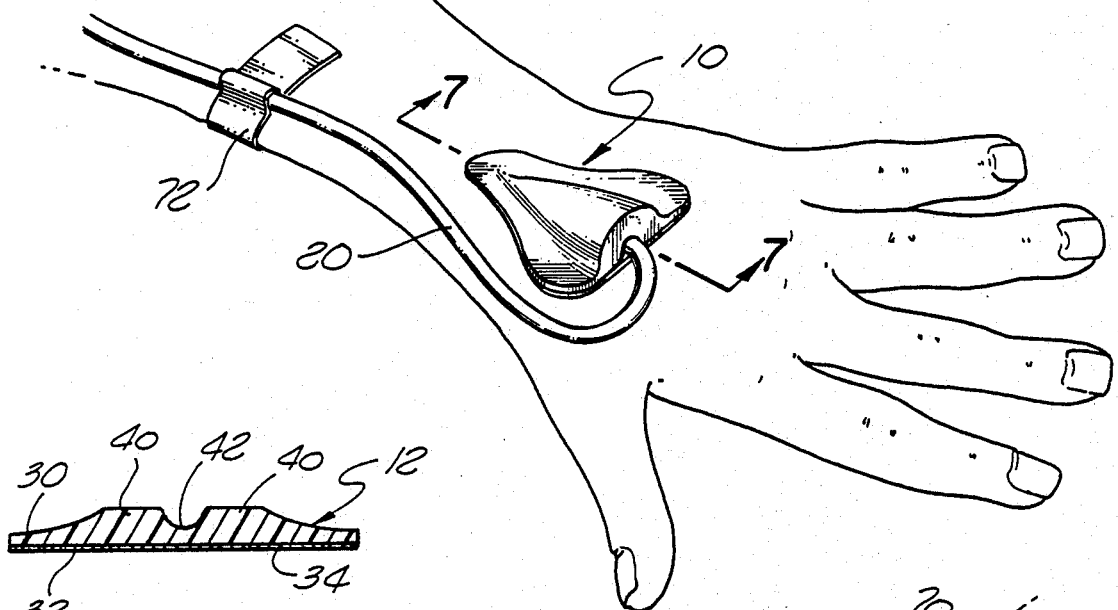
FIG. 1
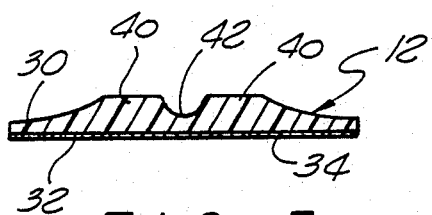
FIG. 3
FIG. 5
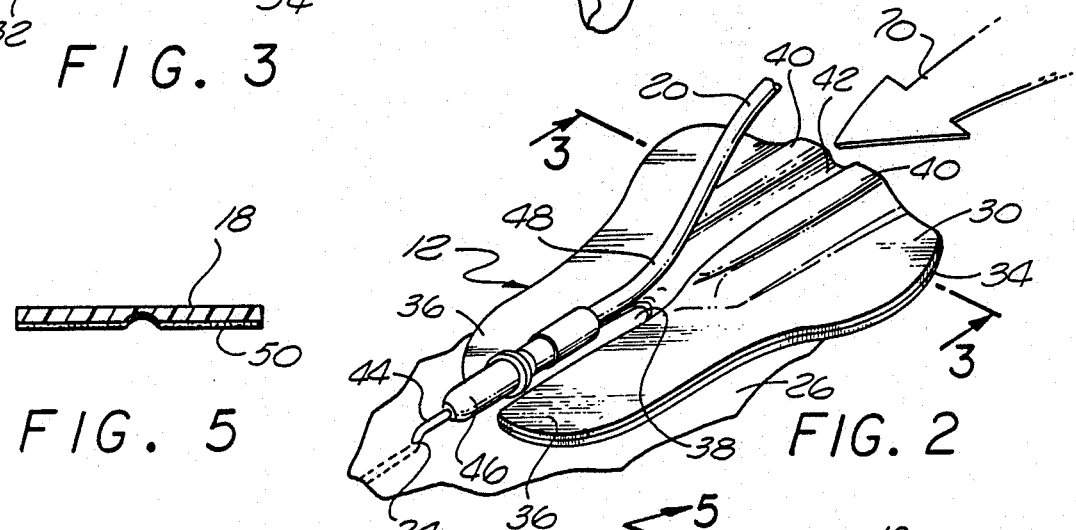
FIG. 2
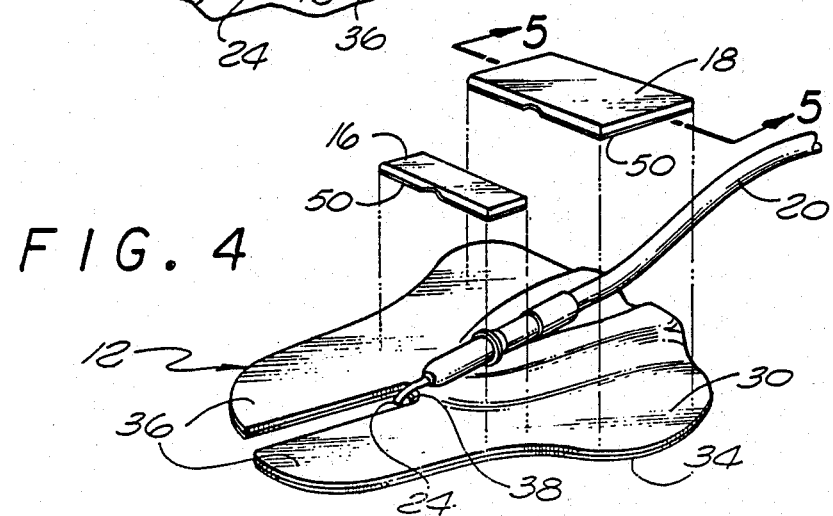
FIG. 4

INTRAVENOUS LINE STABILIZING DEVICE

BACKGROUND OF THE INVENTION

This invention relates generally to a medical apparatus for fastening a tube to a part of a body. More specifically, this invention relates to an intravenous line stabilizing device for securing a catheter on the body adjacent to an incision site in a manner minimizing movement of the catheter with respect to a vein.

Many intravenous lines are placed into patients in hospitals every week. A venipuncture can be made in many areas of the body, such as the forearm, back of the hand, upper arm, scalp, ankle or foot. In this procedure, a catheter is normally inserted into a vein by means of a hollow needle which is then withdrawn to avoid damage to the walls of the punctured vein. The catheter remains attached to the patient and is connected to a source of infusion liquid. It is then necessary to stabilize the catheter to prevent movement which may work the catheter loose and create a potential source of infection or irritation to the patient at the point of catheter insertion. This stabilization is generally done by taping the catheter hub and associated tube fittings to the patient's skin in an area adjacent to the point of catheter insertion.

Although it is important to obtain secure stabilization of the inserted catheter, many medical personnel do not have the skill to make a proper stabilizer using ordinary hospital self-adhesive tape. Even when the medical personnel have sufficient skill, such ordinary tape does not work well since it is too pliable and pulls off the skin too easily.

In recognition of this problem, there have been several prior devices which attempt to make stabilization of the catheter adjacent the insertion point an easier matter for medical personnel. Some of these prior devices are pre-manufactured kits which simplify the process of applying adhesive tape to the catheter. Other prior devices manufactured of plastics or the like include holding mechanisms for minimizing the possibility of an inadvertent catheter withdrawal from the patient. None of the prior devices, however, adequately stabilizes the intravenous line with respect to both the overlying skin and underlying vein. This is important to prevent even minor movement of the catheter within the vein, which movement may cause phlebitis and/or infiltration of the intravenous line.

Accordingly, there has been a need for a novel intravenous line stabilizing device which is of simplified construction, inexpensive to manufacture, and easy to be understood and used by medical personnel. Such a device is also needed which holds the catheter, the vein into which the catheter is inserted, and the overlying skin of the patient in a fixed relationship to minimize movement of the catheter with respect to the vein. Additionally, an intravenous line stabilizing device is needed which can shield the insertion point and adjacent portions of the catheter from externally applied impact forces. Further, a device is needed which provides maximum stabilization between the intravenous line and the body, while minimizing stress and tension on the intravenous line itself. The present invention fulfills these needs and provides other related advantages.

SUMMARY OF THE INVENTION

The present invention resides in an improved clamp for holding an article to an object, which is compact, easy to manufacture, and which provides superior protection for the article when clamped to the object. The clamp comprises, generally, base means for adhering the clamp to the object, and means for fastening the article to an upper surface of the base means. Cover means are provided for overlying at least portions of the base means and the article.

In a preferred form of the invention, the clamp provides a device for affixing a medical tube or the like, to a body. The base means includes a transparent base plate which is contourable to the shape of a part of the body. The base plate is utilized to attach the device to the body, and includes an upper surface, a lower surface, an adhesive backing to the lower surface, and two limbs which adjoin one another at a crotch. The two limbs of the base plate are generally equidistantly spaced from one another to permit positioning of the base plate on the body such that the limbs are caused to lie astride each side of a vein. A medical tube or intravenous line, when secured to the device, preferably extends through the skin at the crotch of the base plate.

The fastening means, in the preferred embodiment, comprises means for securing the medical tube to the upper surface of the base plate. The securing means includes a first cushioned strap having an adhesive backing, which is fastened to the base plate over the medical tube adjacent to the base plate crotch. A second cushioned strap is also provided which has an adhesive backing and is fastened to the base plate over the medical tube.

The cover means is preferably formed of a transparent material and is dimensioned to overlie at least a portion of the base plate and the medical tube. The cover means includes a sealed air compartment between the cover upper and lower surfaces, which air compartment is placed over the medical tube for shielding the covered portion from externally applied impact forces. The cover means also includes a tunnel for the medical tube when the cover is adhered to the base plate. The tunnel includes a cover crotch which is positioned directly over the base crotch in order to minimize pressure and impact forces applied to the medical tube at that point.

When the cover means is adhered to the upper surface of the base plate in a manner covering at least a portion of the medical tube, the cover means provides a continuous bridging surface between the two adjacent base plate limbs. The effect of providing such a continuous bridging surface is to minimize movement of the limbs with respect to one another and with respect to the intermediate vein.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective environmental view of an intravenous line stabilizing device embodying the invention, illustrating the device as applied to the hand of a patient over a catheter insertion site;

FIG. 2 is a perspective assembly view illustrating the manner in which a base plate is positioned with respect to the catheter insertion site;

FIG. 3 is a sectional view of the base plate taken generally along the line 3—3 of FIG. 2;

FIG. 4 is a further perspective assembly view similar to FIG. 2, illustrating the manner in which cushioned adhesive straps are applied over an intravenous line and to the upper surface of the base plate to hold the intravenous line in place within a tapered channel;

FIG. 5 is a sectional view of a cushioned adhesive strap, taken generally along the line 5—5 of FIG. 4;

DETAILED DESCRIPTION OF THE PREFERRED EMBODIMENT

Figure 6:
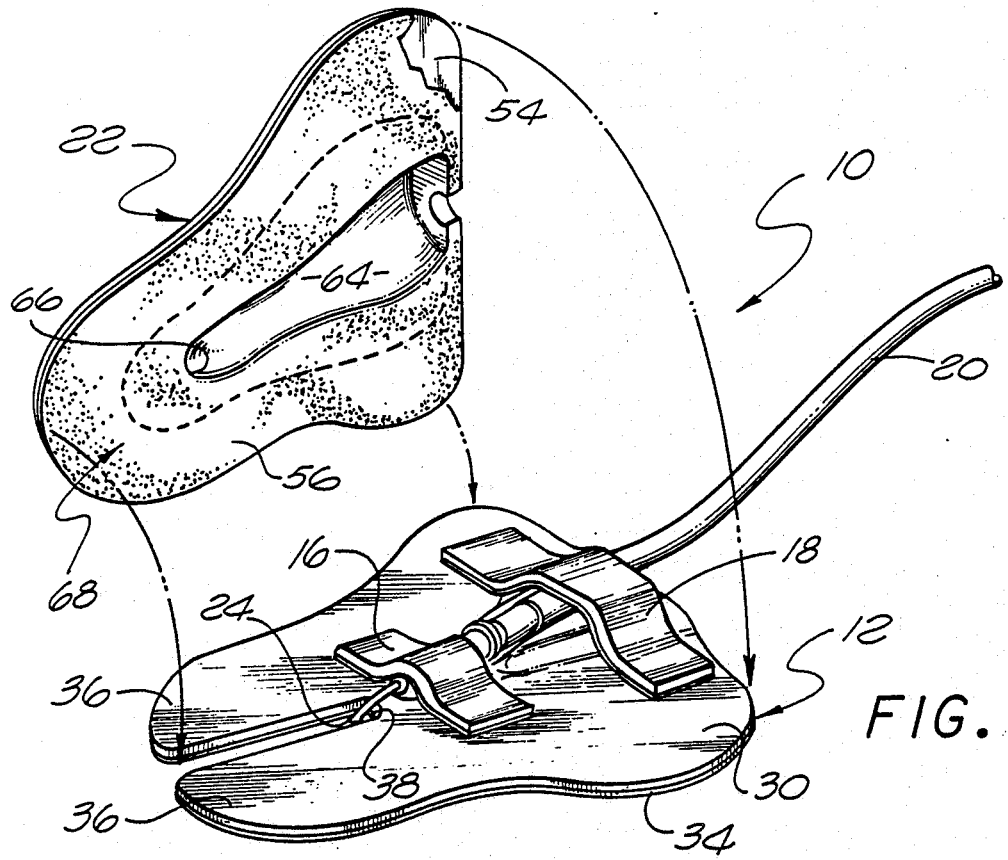
FIG. 6 is a third perspective assembly view similar to FIGS. 2 and 4, illustrating the manner in which a stabilizer cover is placed over and adhered to the base plate.
Figure 8:
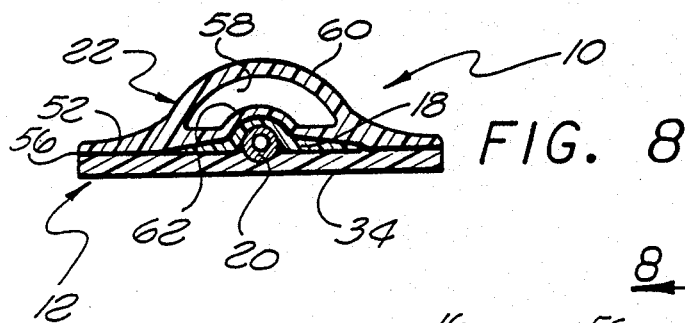
FIG. 8 is a sectional view taken generally along the line 8—8 of FIG. 7, further illustrating the manner in which the intravenous line stabilizing device positions an intravenous line adjacent a catheter insertion site and protects the same against externally applied impact forces.

As shown in the drawings for purposes of illustration, the present invention is concerned with an improved intravenous line stabilizing device, generally designated in the accompanying drawings by the reference number 10. The stabilizing device 10 comprises, generally, a base plate 12 which is contourable to the shape of the body 14, straps 16 and 18 which secure a medical tube 20 to the base plate, and a cover 22 which overlies the base plate and a portion of the tube.

In accordance with the present invention, and as illustrated with respect to a preferred embodiment in FIGS. 1 through 8, the intravenous line stabilizing device 10 is configured for placement on the body 14 in a manner surrounding the insertion site 24 of the medical tube 20 through the skin 26 and into a vein 28. Proper placement of the stabilizing device 10 not only secures the medical tube 20 adjacent to the insertion site 24, but also tends to minimize movement of the catheter within the vein 28.

The base plate 12 and the cover 22 are preferably constructed of a moderately pliable material, for example plastic, that can be readily contoured to the skin of a patient's leg, abdomen, chest, hand, etc. but which is of sufficient bulk and rigidity to resist elastic deformation. In this regard, it is preferred that the base plate 12 and the cover 22 be formed of a clear plastic sheet material approximately 50 to 100 mils thick, minimum.

The base plate 12 provides the component for attaching the stabilizing device 10 to the body 14, and includes an upper surface 30, a lower surface 32, an adhesive backing 34 to the lower surface 32, and two limbs 36 which adjoin one another at a crotch 38. The thickness of the adhesive layer 34 applied to the lower surface 32 of the base plate 12 is exaggerated in the drawings for purposes of illustration. Other adhesive layers to be discussed herein are similarly exaggerated for purposes of clarity. Preferably a peal-off backing strip (not shown) is provided to cover the entire undersurface of the base plate 12, and specifically the adhesive layer 34. This peel-off strip is removed from the adhesive layer 34 just before use of the stabilizing device 10.

The limbs 36 of the base plate 12 are spaced from one anther to permit positioning of the base plate on the body 14 such that the limbs are caused to lie astride each side of the vein 28. In this regard, the spacing between the limbs 36 must be sufficient to allow such positioning without overlapping the limbs onto the vein 28. The upper surface 30 of the base plate 12 includes raised portions 40 which form a tapered channel 42 into which the medical tube 20 is positioned. The tapered channel 42 provide a gently inclined surface on which the medical tube is positioned, between the insertion site 24 and the opposite end of the channel.

The medical tube 20 is illustrated as a catheter assembly which includes a flexible hollow intravenous catheter 44 and a hub 46 of a larger diameter than the catheter insertable portion 44. The catheter assembly also includes a stiff outer tube 48 of larger diameter than the insertable intravenous catheter 44 and of lesser diameter than the hub 46. Thus a standard catheter assembly is described.

Figure 7:
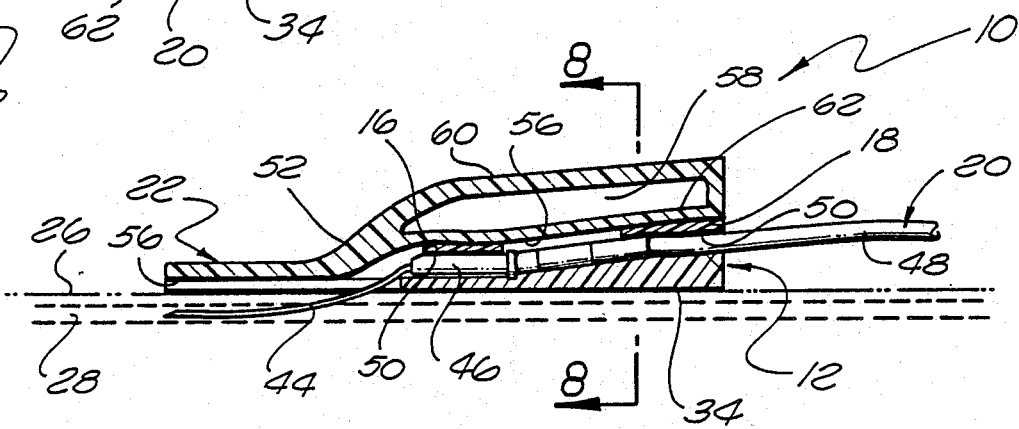
FIG. 7 is an enlarged sectional view taken generally along the line 7—7 of FIG. 1 illustrating the provision of a sealed air compartment within the stabilizer cover and the manner in which the intravenous line is positioned by the device.

The straps 16 and 18 are utilized to secure the medical tube 20 to the upper surface 30 of the base plate 12, and include a smaller strap 16 and a larger strap 18. Each of the straps 16 and 18 are preferably formed of a cushioned, transparent material having an adhesive backing 50 which is covered by a peel-off backing strip (not shown). The smaller strap 16 is fastened to the upper surface 30 of the base plate and over the medical tube adjacent to the base plate crotch 38. As illustrated in FIGS. 4 and 7, the smaller strap 16 is placed over the hub 46. In a similar manner the larger strap 18 is fastened over the raised portions 40 of the base upper surface 30, and over the adjacent portion of the medical tube 20. These straps 16 and 18 securely fix the medical tube 20 within the tapered channel 42 on the upper base surface 30.

The cover 22 includes an upper surface 52, a lower surface 54, and an adhesive backing 56 applied to the lower surface 54. Again, a peel-off backing strip (not shown) is provided over the entire adhesive backing 56, and is removed prior to fixing the cover 22 to the upper surface of the base plate 12. A sealed air compartment 58 is provided between the cover upper and lower surfaces 52 and 54, and is preferably formed at the time the cover 22 is molded. Thus, the cover 22 includes an air dome 60 which overlies the air compartment 58, and an air compartment floor 62.

The cover lower surface 54 is configured to provide a tunnel 64 for the medical tube 20 when the cover 22 is adhered to the base plate 12. The tunnel 64 includes a cover crotch 66 which is positioned directly over the base crotch 38 in order to minimize pressure and impact forces applied to the medical tube at that point. The sealed air compartment 58 is positioned within the cover 22 for placement over the medical tube 20, to shield the covered portion of the medical tube from externally applied impact forces.

The outer dimensions of the cover 22 are made to conform closely with the outer dimensions of the base plate 12. In this manner, the cover 22 can be fixed to the upper surface of the base plate 12 and give the appearance of an integral unit. The portion 68 of the cover lower surface 54 extending from the cover crotch 66 opposite the tunnel 64, is generally flat to maximize contact between that portion of the cover 22 and the base plate limbs 36. When this portion 68 of the cover 22 is adhered to the upper surface of the limbs 36, a continuous bridging surface is formed over the limbs which minimizes movement of the limbs with respect to one another, thereby forming a more rigid stabilizer.

Prior to utilizing the intravenous line stabilizing device 10, the skin is prepared by cleaning the area that will receive the intravenous catheter 44 and the stabilizing device. Often it is necessary to shave the patient's hair off the body part, and apply tincture of benzoin. Next, the intravenous catheter is started in the standard fashion to place the catheter 44 within the vein 28 so that it extends through the insertion site 24.

The peel-off strip (not shown) is then removed from the adhesive layer 34, and the base plate 12 is positioned below the medical tube 20 as indicated by the arrow 70 in FIG. 2. The base plate 12 is positioned completely under the medical tube 20 so that the base crotch 38 is generally adjacent to the insertion site 24. Next, the medical tube 20 is placed within the tapered channel 42, and the smaller strap 16, having its peel-off backing strip removed, is applied over the hub 46. The large strap 18 is then also applied to the upper surface 30 of the base plate 12 over the medical tube 20 and the raised portions 40 of the base upper surface 30 (see FIG. 4).

The adhesive backing 56 of the cover 22 is exposed, and the lower surface 54 of the cover is placed over the base plate upper surface 30, the straps 16 and 18, and the adjacent portion of the medical tube 20 (see FIG. 6). As mentioned previously, the portion 68 of the cover is placed over the limbs 36 to form a continuous bridging surface. The cover crotch 66 is placed generally directly over the base crotch 38, and the tunnel 64 is placed over the portion of the medical tube held within the tapered channel 42.

Finally, the patient's arm may be secured to an arm band if necessary, and the medical tube 20 may be secured to the arm of the patient with common dressing tape 72.

From the foregoing it is to be appreciated that the improved intravenous line stabilizing device 10 of the present invention provides maximum stabilization between the medical tube 20 and body 14, while minimizing stress and tension on the medical tube itself. In particular, relative movement of the intravenous line catheter 44 within the vein 28 is minimized, thus reducing the possibility of phlebitic and/or infiltrated veins. By the use of transparent, relatively inelastic yet contourable materials, the stabilizing device 10 can adapt to virtually any body part, yet provide sufficient rigidity to accomplish its purpose in creating an "integral" unit between the vein 28, the overlying skin 26 and medical tube 20. The stabilizing device 10 is quite easy to use by medical personnel, and provides the additional advantages of shielding the intravenous catheter 44 and the adjacent portions of the medical tube 20 from externally applied impact forces, thus further protecting the insertion site 24.

Although a particular embodiment of the invention has been described in detail for purposes of illustration, various modifications may be made without departing from the spirit and scope of the invention. Accordingly, the invention is not to be limited, except as by the appended claims.

I claim:

1. An intravenous line stabilizing device, comprising:
    base means for adhering the stabilizing device to a part of a body, the base means including an upper surface, a lower surface, and a plurality of limbs, wherein two adjacent limbs adjoin one another at a crotch;
    means for securing an intravenous line to the upper surface of the base means; and
    cover means for overlying at least portions of the base means and the intravenous line, the cover means being adhered to the upper surface of the base means in a manner providing a continuous bridging surface between the two adjacent limbs, wherein the cover means includes cushion means for shielding the covered portion of the intravenous line from externally applied impact forces.

2. A device as set forth in claim 1, wherein the base means is formed of a transparent material which is contourable to the shape of the part of the body.

3. A device as set forth in claim 1, wherein the upper surface of the base means includes a tapered channel into which the intravenous line is positioned.

4. A device as set forth in claim 1, wherein the securing means includes a first cushioned strap having an adhesive backing which is fastened to the base means and over the intravenous line adjacent to the crotch of the base means.

5. A device as set forth in claim 4, wherein the securing means includes a second cushioned strap having an adhesive backing which is fastened to the base means and over the intravenous line.

6. A device as set forth in claim 1, wherein the cover means is formed of a transparent material which is contourable to the shape of the part of the body.

7. A device as set forth in claim 1, wherein the cover means includes an upper surface, a lower surface, and an air compartment between the cover upper and lower surfaces, the sealed air compartment providing the cushion means for shielding the covered portion of the intravenous line from externally applied impact forces.

8. A device as set forth in claim 7, wherein the lower surface of the cover means forms a tunnel for the intravenous line when the cover is adhered to the base means, wherein the tunnel includes a cover crotch which is positioned directly over the base crotch in order to minimize pressure on the intravenous line at that point.

9. A device as set forth in claim 1, wherein the two adjacent limbs of the base means are spaced from one another to permit positioning of the base means on the part of the body such that the limbs are caused to lie astride each side of a vein, and wherein the intravenous line extends through the skin at the crotch of the base means.

10. A clamp for holding an article to an object, comprising:
    base means for adhering the clamp to the object, including an upper surface, a lower surface, and a plurality of limbs, wherein two adjacent limbs adjoin one another at a crotch;
    means for fastening the article to the upper surface of the base means; and
    cover means for overlying at least portions of the base means and the article, the cover means including an upper surface, a lower surface, and an adhesive backing to the lower surface, wherein the lower cover surface is adhered to the upper base surface in a manner providing a continuous bridging surface between the two adjacent limbs.

11. A clamp as set forth in claim 10, wherein the base means is formed of a transparent material which is contourable to the shape of the object, and the upper surface of the base means includes a channel into which the article is positioned.

12. A clamp as set forth in claim 10, wherein the clamp is configured for affixing a medical tube or the like to a body such that the two adjacent limbs of the base means are spaced from one another to permit positioning of the base means on the body such that the limbs are caused to lie astride each side of a vein, and wherein the medical tube extends through the skin at the crotch of the base means.

13. A clamp as set forth in claim 10, wherein the fastening means includes a plurality of cushioned straps having adhesive backings, which are fastened to the base means and over the article.

14. A clamp as set forth in claim 10, wherein the lower surface of the cover means forms a tunnel for the article when the cover is adhered to the base means, wherein the tunnel includes a cover crotch which is positioned directly over the base crotch.

15. A clamp as set forth in claim 10, wherein the cover means includes a sealed air compartment between the cover upper and lower surfaces.

16. An intravenous line stabilizing device, comprising:
a base plate contourable to the shape of a part of a body, for attaching the stabilizing device to the body, the base plate having an upper surface and a lower surface;
means for securing an intravenous line to the upper surface of the base plate, including removable tape means; and
a cover for overlying at least a portion of the base plate and the intravenous line, the cover including an upper surface, a lower surface, an adhesive backing to the lower surface, and an air compartment between the cover upper and lower surfaces, wherein the lower cover surface is adhered to the upper base surface in a manner placing the sealed air compartment over the intravenous line.

17. A device as set forth in claim 16, wherein the base plate includes two limbs which adjoin one another at a crotch, wherein the two adjacent limbs of the base plate are spaced from one another to permit positioning of the base plate on the part of the body such that the limbs are caused to lie astride each side of a vein, and wherein the intravenous line extends through the skin at the crotch of the base plate.

18. A device as set forth in claim 17, wherein the upper surface of the base plate includes a channel into which the intravenous line is positioned.

19. A device as set forth in claim 17, wherein the removable tape means includes a first cushioned strap having an adhesive backing which is fastened to the base plate and over the intravenous line adjacent to the crotch of the base plate, and a second cushioned strap having an adhesive backing which is fastened to the base plate and over the intravenous line.

20. A device as set forth in claim 17, wherein the cover is adhered to the upper surface of the base plate in a manner providing a continuous bridging surface between the limbs.

21. A device as set forth in claim 20, wherein the lower surface of the cover forms a tunnel for the intravenous line when the cover is adhered to the base plate, wherein the tunnel includes a cover crotch which is positioned directly over the base crotch.

22. A device for affixing a medical tube to a body, comprising:
a base plate contourable to the shape of a part of the body, for attaching the device to the body, the base plate having an upper surface, a lower surface, an adhesive backing to the lower surface, and two limbs which adjoin one another at a crotch, wherein the upper surface of the base plate includes a tapered channel into which the medical tube is placed, and wherein the limbs are spaced from one another to permit positioning of the base plate on the part of the body such that the limbs are caused to lie astride each side of a vein;
means for securing the medical tube to the upper surface of the base plate within the tapered channel, the securing means including a first cushioned strap having an adhesive backing which is fastened to the base plate over the medical tube adjacent to the crotch of the base plate, and a second cushioned strap having an adhesive backing which is fastened to the base plate over the tapered channel; and
cover means for overlying at least a portion of the base plate and the medical tube, the cover means including an upper surface, a lower surface, an adhesive backing to the lower surface, and an air compartment between the cover upper and lower surfaces, wherein the lower cover surface is adhered to the upper base surface in a manner placing the air compartment over the medical tube for shielding the covered portion of the medical tube from externally applied impact forces, the cover means further being adhered to the upper surface of the base plate in a manner providing a continuous bridging surface between the limbs, and wherein the lower surface of the cover means forms a tunnel for the medical tube when the cover means is adhered to the base plate, the tunnel including a cover crotch which is positioned directly over the base crotch.

* * * * *